(12) United States Patent
Arefieg

(10) Patent No.: US 9,358,334 B2
(45) Date of Patent: Jun. 7, 2016

(54) INTEGRATED GLUCOSE MONITOR AND INSULIN INJECTION PEN WITH AUTOMATIC EMERGENCY NOTIFICATION

(75) Inventor: Rana J. Arefieg, Ridgefield, CT (US)

(73) Assignee: THUBAN, INC., Ridgefield, CT (US)

(*) Notice: Subject to any disclaimer, the term of this patent is extended or adjusted under 35 U.S.C. 154(b) by 275 days.

(21) Appl. No.: 13/472,648

(22) Filed: May 16, 2012

(65) Prior Publication Data

US 2012/0238853 A1 Sep. 20, 2012

Related U.S. Application Data

(63) Continuation of application No. 12/806,669, filed on Aug. 18, 2010, now Pat. No. 8,206,340.

(51) Int. Cl.
*A61M 5/142* (2006.01)
*A61B 5/00* (2006.01)
(Continued)

(52) U.S. Cl.
CPC .......... *A61M 5/14244* (2013.01); *A61B 5/0022* (2013.01); *A61B 5/14532* (2013.01); *A61B 5/157* (2013.01); *A61B 5/4839* (2013.01); *A61M 5/1723* (2013.01); *A61B 5/1112* (2013.01); *A61B 5/741* (2013.01); *A61B 5/747* (2013.01); *A61B 5/749* (2013.01); *A61M 5/31546* (2013.01);
(Continued)

(58) Field of Classification Search
CPC .............. A61M 5/172; A61M 5/1723; A61M 5/14566; A61M 5/152; A61M 5/148; A61M 5/2033; A61M 5/1483; A61M 5/2053; A61M 5/14244; A61M 5/1456; A61M 1/0011; A61M 1/0076; A61M 2005/2013; A61M 3/0237; A61M 3/0233; A61C 17/0214; A61D 1/025
USPC ...................... 604/65–67, 131–155
See application file for complete search history.

(56) References Cited

U.S. PATENT DOCUMENTS 4,226,235 A   10/1980   Sarnoff et al.
4,329,988 A   5/1982    Sarnoff et al.
(Continued)

FOREIGN PATENT DOCUMENTS

EP   1102194   5/2001

OTHER PUBLICATIONS

Humapen Memoir Insulin Delivery Device User Manual, Eli Lily & Company., 2006.
(Continued)

*Primary Examiner* — Scott Medway
(74) *Attorney, Agent, or Firm* — David M. Quinlan, P.C.

(57) ABSTRACT

An insulin injection pen and blood glucose monitoring device is integrated into a single unit that fits in a user's clothing pocket or handbag. The device includes a blood glucose monitoring system for detecting the user's blood glucose level, an insulin injection mechanism, and a microprocessor that calculates an insulin dosage appropriate to the detected blood glucose level of a particular user and sets the insulin injection mechanism to administer the calculated insulin dosage. The device automatically informs a remote emergency service provider if the microprocessor determines that the detected blood glucose level presents a potential danger to the user. The microprocessor also calculates treatment regimens based on the detected blood glucose level and displays the treatment regimens on an LCD display. The device can include a GPS receiver that detects the location of the device, which is transmitted by the device to the remote emergency service.

20 Claims, 9 Drawing Sheets

(51) Int. Cl.
*A61B 5/145* (2006.01)
*A61B 5/157* (2006.01)
*A61M 5/172* (2006.01)
*A61B 5/11* (2006.01)
*A61M 5/315* (2006.01)

(52) U.S. Cl.
CPC ............... *A61M 2205/3523* (2013.01); *A61M 2205/3553* (2013.01); *A61M 2205/3576* (2013.01); *A61M 2205/50* (2013.01)

(56) References Cited

U.S. PATENT DOCUMENTS

| | | | |
|---|---|---|---|
| 4,578,064 | A | 3/1986 | Sarnoff et al. |
| 4,731,726 | A | 3/1988 | Allen |
| 5,019,974 | A | 5/1991 | Beckers |
| 5,536,249 | A | 7/1996 | Castellano |
| 5,593,390 | A | 1/1997 | Castellano |
| 5,728,074 | A | 3/1998 | Castellano |
| 5,822,715 | A | 10/1998 | Worthington |
| 5,840,020 | A | 11/1998 | Heinonen |
| 5,925,021 | A | 7/1999 | Castellano |
| 6,021,392 | A | 2/2000 | Lester et al. |
| 6,175,752 | B1 | 1/2001 | Say et al. |
| 6,192,891 | B1 | 2/2001 | Gravel et al. |
| 6,302,855 | B1 | 10/2001 | Lav et al. |
| 6,544,212 | B2 | 4/2003 | Galley et al. |
| 6,875,195 | B2 | 4/2005 | Choi |
| 6,906,802 | B2 | 6/2005 | Voelkel |
| 6,996,538 | B2 | 2/2006 | Lucas |
| 7,404,796 | B2 | 7/2008 | Ginsberg |
| 7,427,275 | B2 | 9/2008 | DeRuntz et al. |
| 7,534,230 | B2 | 5/2009 | Follman et al. |
| 7,591,801 | B2 | 9/2009 | Brauker et al. |
| 7,737,858 | B2 | 6/2010 | Matityaho |
| 7,871,393 | B2 | 1/2011 | Monroe |
| 7,988,630 | B1 | 8/2011 | Osorio et al. |
| 8,044,778 | B2 | 10/2011 | Monroe |
| 8,149,111 | B2 | 4/2012 | Monroe |
| 8,361,026 | B2 | 1/2013 | Edwards et al. |
| 8,366,682 | B2 | 2/2013 | Wyrick |
| 2002/0013522 | A1 | 1/2002 | Lav et al. |
| 2002/0016719 | A1 | 2/2002 | Nemeth et al. |
| 2005/0075954 | A1 | 4/2005 | Matsumoto et al. |
| 2006/0135874 | A1 | 6/2006 | Peng |
| 2006/0173406 | A1 | 8/2006 | Hayes et al. |
| 2007/0055586 | A1 | 3/2007 | Lucas |
| 2007/0066938 | A1 | 3/2007 | Iio et al. |
| 2007/0197968 | A1* | 8/2007 | Pongpairochana et al. .. 604/131 |
| 2008/0119705 | A1 | 5/2008 | Patel et al. |
| 2008/0269673 | A1 | 10/2008 | Butoi et al. |
| 2008/0306434 | A1 | 12/2008 | Dobbles et al. |
| 2009/0105570 | A1 | 4/2009 | Sloan et al. |
| 2009/0137957 | A1 | 5/2009 | Wagener |
| 2009/0138207 | A1 | 5/2009 | Cosentino et al. |
| 2010/0010330 | A1 | 1/2010 | Rankers et al. |
| 2010/0016700 | A1 | 1/2010 | Sieh et al. |
| 2010/0090004 | A1 | 4/2010 | Sands et al. |
| 2010/0141457 | A1 | 6/2010 | Wass et al. |
| 2010/0256593 | A1 | 10/2010 | Yodfat et al. |
| 2011/0082711 | A1 | 4/2011 | Poeze et al. |
| 2011/0184264 | A1 | 7/2011 | Galasso et al. |
| 2011/0282173 | A1 | 11/2011 | Fonduca et al. |
| 2011/0320130 | A1 | 12/2011 | Valdes et al. |
| 2012/0047049 | A1 | 2/2012 | Cadiz |
| 2012/0173287 | A1 | 7/2012 | Cowand |
| 2012/0203566 | A1 | 8/2012 | Kidd et al. |
| 2012/0278228 | A1 | 11/2012 | Rubinstein |
| 2014/0142507 | A1 | 5/2014 | Armes |

OTHER PUBLICATIONS

"A New Era in Blood Glucose Monitoring Begins: The Accu-Chek Mobile System," Trade News, Vienna, Austria, Roche Diabetes Care, Sep. 30, 2009.

Walsh, J., "Concept 2: The Smart Insulin Pen," www.diabetesnet.com/diabetes_technology/smart_pen.php (last visited Mar. 25, 2010).

International Search Report and Written Opinion, dated Oct. 31, 2011 in PCT Appln. No. PCT/US11/01349.

Thomas Seth. "Tin Lifesaver for a Growing Worry," New York Times. Sep. 8, 2012, pp. B1-B2.

International Search Report and Written Opinion, dated Mar. 20, 2015, in PCT Appln. No. PCTUS14/16648.

\* cited by examiner

INTEGRATED GLUCOSE MONITOR AND INSULIN INJECTION PEN WITH AUTOMATIC EMERGENCY NOTIFICATION

BACKGROUND OF THE INVENTION

1. Field of the Invention

The present invention relates to managing diabetes symptoms, and more particularly, to a device and method for controlling diabetes symptoms and monitoring a diabetes patient.

2. Description of Related Art

The prior art includes devices for monitoring blood glucose levels of diabetes patients and devices for administering insulin to control blood glucose levels. Known blood glucose monitors take many forms. For example, one type of monitor is implanted in a patient and transmits blood glucose readings to an external display more or less continuously. Other devices require the patient to take periodic blood samples for analysis by the glucose monitor. In the latter type of device the patient typically lances a finger and places a blood sample on a medium such as a test strip. The monitor analyzes the test strip and provides a digital readout of the blood glucose level on a monitor display.

Depending on the patient's blood glucose level, it may or may not be necessary to administer a dose of insulin. Insulin delivery devices also take many forms. Broadly speaking, insulin delivery can be either essentially automatic by permanently attaching the patient to an insulin pump, or as-needed by using an injection device (such as a hypodermic needle) with which the patient injects an amount of insulin determined according to a predetermined protocol when the measured blood glucose level is outside an acceptable range.

Many devices and systems seek to automate diabetics' blood glucose control protocols by computerizing conventional devices so that insulin dosages can be automatically determined and delivered with minimum intervention by the patient. The following references illustrate some typical examples of such devices and systems:

---

U.S. Pat. No. 4,731,726
U.S. Pat. No. 5,019,974
U.S. Pat. No. 5,536,249
U.S. Pat. No. 5,593,390
U.S. Pat. No. 5,728,074
U.S. Pat. No. 5,822,715
U.S. Pat. No. 5,840,020
U.S. Pat. No. 5,925,021
U.S. Pat. No. 6,192,891
U.S. Pat. No. 6,544,212
U.S. Pat. No. 6,875,195
U.S. Pat. No. 6,906,802
U.S. Pat. No. 7,427,275
U.S. Pat. No. 7,534,230
U.S. Pat. No. 7,591,801
U.S. Publ. No. 2008/0306434
U.S. Publ. No. 2010/0010330
European. App. No. 1 102 194

---

Devices disclosed in U.S. Pat. No. 5,728,074 embody the "as-needed" type of insulin delivery approach. Some of these disclosed devices could be particularly useful because they provide a variety of functions that a diabetic would undoubtedly find helpful in managing his or her disease. For example, the disclosed embodiments include devices that combine an insulin injection mechanism and a blood glucose monitor, such as the "pen-type injector" depicted in FIG. 25. This device has at one end a removable cap that conceals a hypodermic needle for insulin injection and a lancet mechanism used by the patient to prick a finger to obtain a blood sample for analysis by a test strip on the injector housing. U.S. Patent Pub. No. 2010/0010330 exemplifies the type of system that employs a blood glucose sensor implanted in the patient to provide continuous glucose level data to a bedside monitoring system that controls an insulin infusion pump. The system can include software that determines if the patient's blood glucose level is at a dangerously low level and can alert 911 or other medical emergency response provider. While this feature enhances patient safety, it has a significant drawback in that the patient is tethered to the monitoring system.

Many diabetics lead relatively active lives, and for them being tethered to a monitoring system is obviously not acceptable. These patients require a treatment regimen that enables them to maintain a normal lifestyle by minimizing limitations that might otherwise be imposed by their diabetes. Even though existing devices and systems permit such patients to closely monitor their own blood glucose levels, and thus minimize the risk of becoming hypoglycemic or hyperglycemic at any given time, a diabetes patient still can experience either condition without much warning. Hypoglycemia can be particularly dangerous because it can impair cognitive functions, so a patient with a low blood glucose level can become disoriented and confused very rapidly. If the patient's blood glucose level is not corrected in time, he or she can lapse into a coma and even die before being able to take necessary corrective action. By the same token, hyperglycemia, while less likely than hypoglycemia to present an emergency situation, can nonetheless be dangerous. Accordingly, devices that rely on the patient to take appropriate steps after determining his or her own blood glucose level would have greater utility if they could automatically take action to preempt the potentially serious consequences of rapid changes in blood glucose levels.

SUMMARY OF THE INVENTION

It is an object of the present invention to improve on known techniques involving self-administration of appropriate therapy to adjust glucose levels after a patient tests his or her own blood glucose level. One important aspect of the invention provides an automatic alert to an emergency service provider if a patient using a device for self-testing his or her own blood glucose level does not respond to prompts and thus may be in need of immediate medical attention.

In accordance with a first aspect of the invention, a portable blood glucose monitoring device and insulin injection pen integrated into a single unit for testing and treating diabetes symptoms in a user comprises a housing of a size suitable for transport in a handbag or clothing pocket of the user, a blood glucose monitoring system within the housing for receiving a sample of the user's blood and detecting the glucose level thereof, an insulin injection mechanism within the housing for permitting the user to self administer an insulin injection, a microprocessor within the housing for calculating an insulin dosage appropriate to the detected blood glucose level and setting the insulin injection mechanism to administer the calculated insulin dosage, a display mounted on the housing for displaying the detected blood glucose level and the calculated insulin dosage, and a communication device within the housing and under the control of the microprocessor for automatically informing a remote emergency service provider if the microprocessor determines that the detected blood glucose level presents a potential danger to the user.

In accordance with more specific embodiments of the invention, such a unit further comprises at least one manual input device operable by the user in conjunction with information displayed on the display for providing a user interface for permitting the user to control predetermined operations of the unit. A particularly advantageous embodiment comprises a GPS receiver within the housing for detecting the location of the device, wherein the communication device transmits information regarding the location to the remote emergency service.

An additional aspect of the invention includes a method of monitoring a diabetes patient including providing a portable blood glucose monitoring device comprising a housing of a size suitable for transport in a handbag or clothing pocket of the patient, the housing having therein a blood glucose monitoring system for receiving a sample of the patient's blood and detecting the glucose level thereof, a storage device for storing a threshold representing a blood glucose level of potential danger to the patient, a GPS receiver for detecting the location of the device, and a communication device for contacting a remote emergency service provider, introducing to the blood glucose monitoring system a sample of the user's blood, comparing the detected blood glucose level of the sample to the threshold blood glucose level, and if the detected level is past the threshold, automatically activating the communication device to transmit a message to the emergency service provider including information on the potentially dangerous condition of the user and information regarding the location of the device.

In accordance with more specific method aspects of the invention, the storage device stores a first threshold representing a blood glucose level below which the patient is severely hypoglycemic and may be disoriented or comatose, and a second threshold above which the patient is severely hyperglycemic and may require immediate medical intervention, and the method further includes setting a time period by which the patient must provide an input to the monitoring device if the detected blood glucose level is below the first threshold or above the second threshold before automatically activating the communication device. In another variation, the monitoring device further comprises an insulin injection mechanism within the housing for permitting the user to self administer an insulin injection, and the method further includes determining if the detected blood glucose level indicates that the patient is hypoglycemic or hyperglycemic, and if the patient is hypoglycemic, instructing the patient to ingest an amount of at least one blood glucose producing substance based on the detected blood glucose level, or if the patient is hyperglycemic, calculating an insulin dosage appropriate to the detected blood glucose level and using the insulin injection mechanism to set an amount of insulin to be injected based on the detected blood glucose level.

BRIEF DESCRIPTION OF THE DRAWINGS

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

FIG. 6, comprising

One skilled in the art will readily understand that the drawings are not strictly to scale, but nevertheless will find them sufficient, when taken with the detailed descriptions of preferred embodiments that follow, to make and use the present invention.

DETAILED DESCRIPTION OF PREFERRED EMBODIMENTS

Figure 1A:
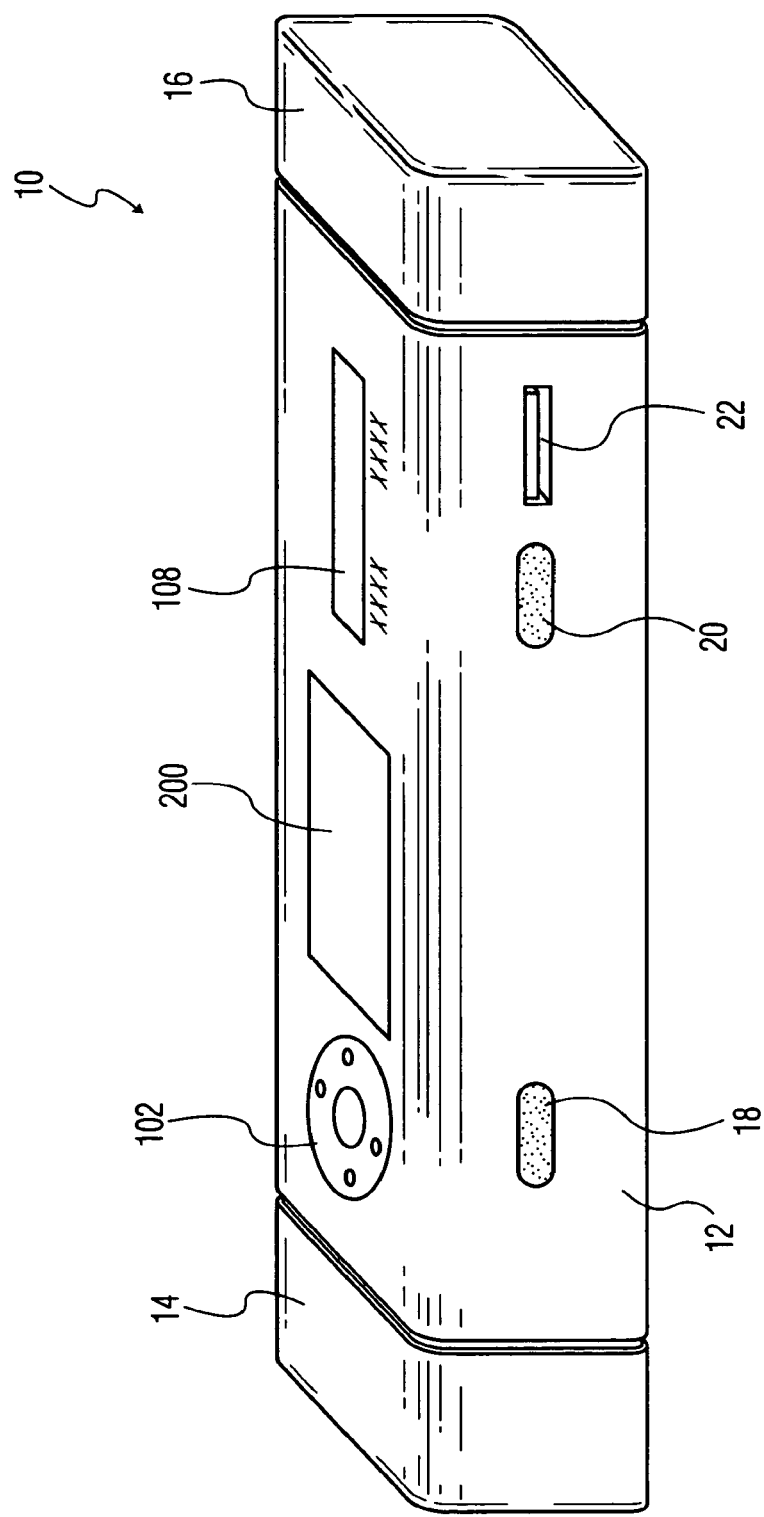
FIGS. 1A and 1B are perspective views showing the four sides of a unitary integrated blood glucose monitor and insulin injection pen according to an embodiment of the present invention.
Figure 1B:
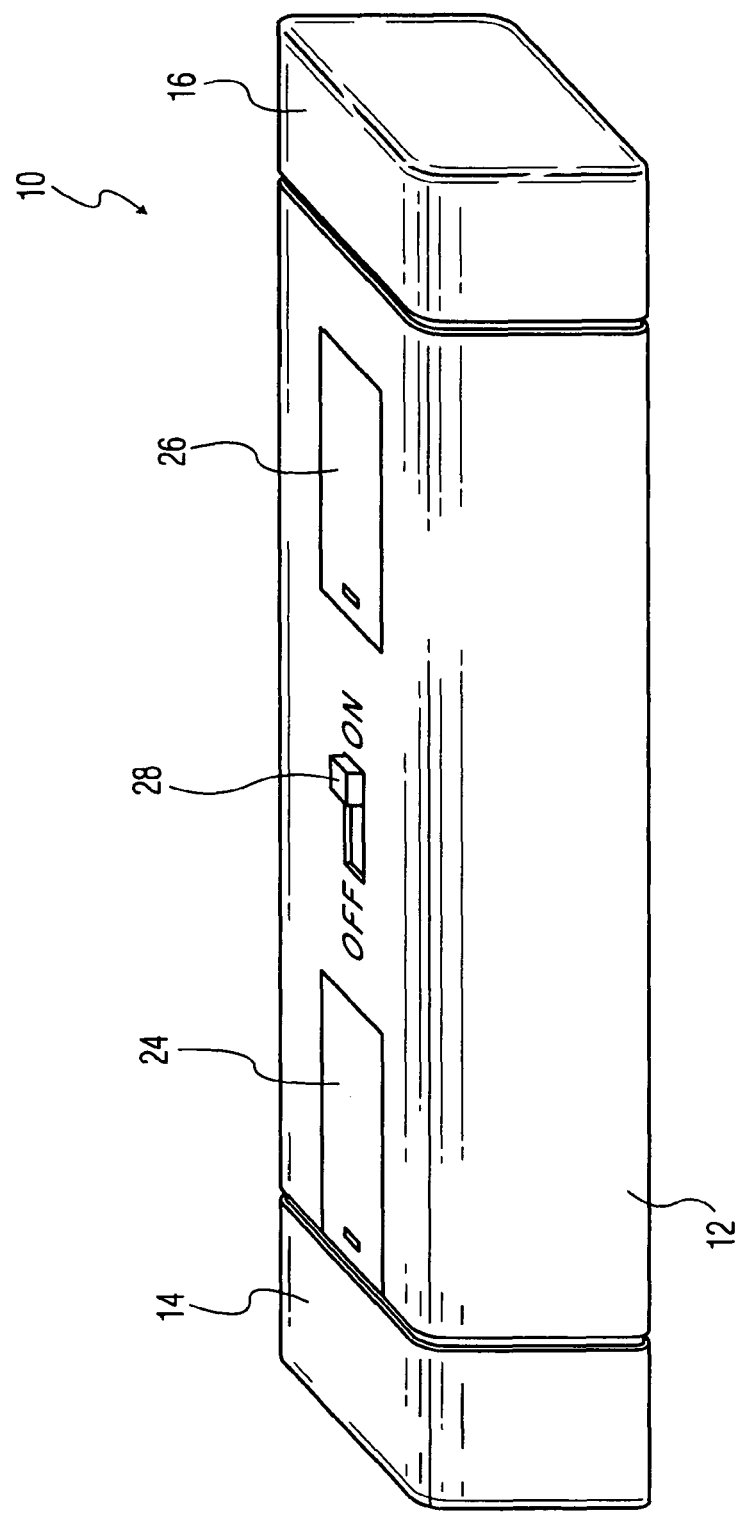

FIGS. 1A and 1B show an integrated blood glucose monitor and insulin pen unit 10 in accordance with one embodiment of the invention. The integrated monitor/pen unit 10 has an elongated, generally rectangular housing 12 most conveniently provided in a one-piece molded plastic construction. A cap 14 fits onto the housing 12 at one end to conceal a hypodermic needle (not shown in FIG. 1) that forms a part of an insulin injection mechanism described in more detail further below. The cap 14 is also conveniently molded from a suitable plastic material in one piece, and fits snugly onto the end of the housing 12 either by friction or by a snap fit, to prevent inadvertent removal of the cap and consequent exposure of the hypodermic needle. A blood glucose monitoring system 16 also includes a cap that fits snugly onto the other end of the housing 12. Further details of the blood glucose monitoring system and the insulin injection mechanism are described below in connection with FIGS. 2 and 3.

When the caps are in place on the housing 12, these parts together form a cylinder with a rectangular cross section that has substantially constant dimensions along its entire length and has a unitary appearance. The cross section can have rounded corners, which will give the unit 10 a compact appearance and facilitate handling by a user. The elongated configuration of the housing enables the various mechanical and electronic components of the monitor/pen unit 10 to be contained in a compact device that is easily carried in a pocket or handbag/purse. To that end, a preferred unit will have a cross section about 1.0"×0.5" and be about 5" to 6" long. Other configurations and dimensions can be used within the broadest scope of the invention. For example, one skilled in the art may chose to arrange the internal components of the unit discussed below in a manner that makes it preferable to use a different configuration or a different size.

The unit 10 further includes various components for receiving inputs from a user and communicating outputs to the user or to other destinations, as described further below. A speaker 18 enables the unit to provide voice commands or prompts to the user, and a microphone 20 enables the user to communicate with the unit by voice. A USB port 22 enables communications between the unit and associated peripheral devices, as well as permitting uploading of information to a memory in the unit and downloading information from the memory. On an adjacent side of the housing a removable cover 24 provides access to the insulin injection mechanism within the housing for purposes described below. On the same side, a battery compartment with a removable cover 26 accepts batteries of a suitable rating for providing operating power to the unit. The batteries can be rechargeable, and recharging can be accomplished by attaching a suitable power cord to the USB port. This side of the housing 12 can be considered the rear of the unit since the covers 24 and 26 are accessed relatively infrequently. The covers 24 and 26 are placed on the longer side of the unit's rectangular cross section to facilitate their manipulation by a user. This side of the unit also includes an ON-OFF switch 28 for powering the unit on and off. (In describing embodiments of the invention, terms indicating direction or orientation, such as "front," "rear," "right," "left," etc., may be used to facilitate the description. They do not imply that the invention is limited to a particular orientation of the pen/monitor unit.)

Figure 2A:
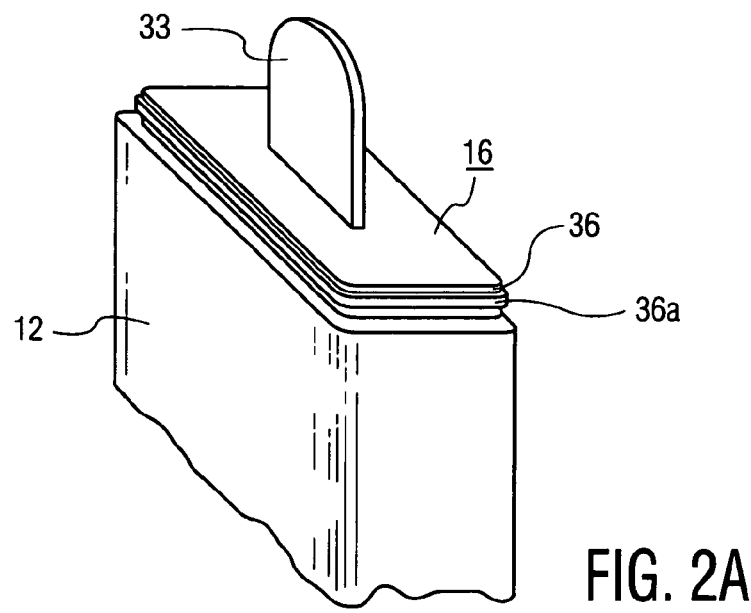
FIGS. 2A and 2B schematically depict a lancet and blood glucose test strip that form a part of a blood glucose monitoring system that is integrated into the blood glucose monitor and insulin pen unit shown in FIG. 1.
Figure 2B:
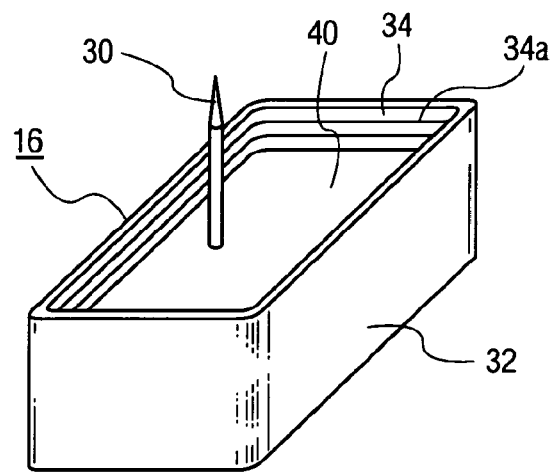

FIGS. 2A and 2B are schematic representations of an exemplary embodiment of the blood glucose monitoring system 16. FIG. 2B shows a lancet 30 extending from the inside of a glucose monitoring system cap 32 that fits snugly on the end of the housing 12 as discussed above. The lancet 30 is essentially a very sharp needle typically made of surgical grade stainless steel. The patient pricks a finger with the lancet to draw a sufficient quantity of blood for glucose level testing. FIG. 2A shows the end of the housing 12 from which extends a glucose test strip 33 onto which the user places a blood sample by touching the lanced finger to the strip. The strip then introduces the blood by capillary action into conventional testing apparatus within the unit that determines the blood's glucose level. The details of the glucose level testing do not form a part of the present invention, and are well known to those skilled in the art. U.S. Pat. No. 5,728,074 mentioned above describes various ways of performing such testing and obtaining a corresponding electrical signal. Any of those techniques, or variations thereof, can be used in performing blood glucose testing with the unit 10, and those portions of U.S. Pat. No. 5,728,074 describing such testing are incorporated by reference as if set out in full herein. Many of the other patents discussed above also describe ways of testing blood glucose levels, and unit 10 could use any of those techniques as well.

Although the manner in which the patient's blood glucose level is determined is conventional, the configuration of the blood glucose testing system 16 shown in FIGS. 2A and 2B is particularly advantageous from the standpoint of a user of the unit 10. The cap 32 has an internal shoulder 34 that fits over a corresponding external shoulder 36 on the housing 12. The internal shoulder 34 includes a circumferential groove 34a that accepts a circumferential ridge 36a on the external shoulder 36. The groove 34a and ridge 36a provide a snap fit to positively hold the cap 32 on the housing 12 The outside peripheral surfaces of the cap 32 and housing 12 are flush in order to maintain the unitary appearance of the unit 10 when the cap is in place on the housing. A lancet 30 and test strip 33 are each typically used only once and then discarded. The cap 32 can be made hollow to store sterile lancets, which are accessible to a user by making an interior panel 40 in the cap removable. Test strips may be stored in a cartridge in the unit and dispensed one at a time by a slider button on the side of the unit (not shown). The end of the unit may be made removable to enable replacement of empty test strip cartridges. Those skilled in the art will recognize many ways in which the blood glucose monitoring system can be implemented while still maintaining the sleek, compact appearance of the unit 10 that comprises an aspect of the invention.

Figure 3:
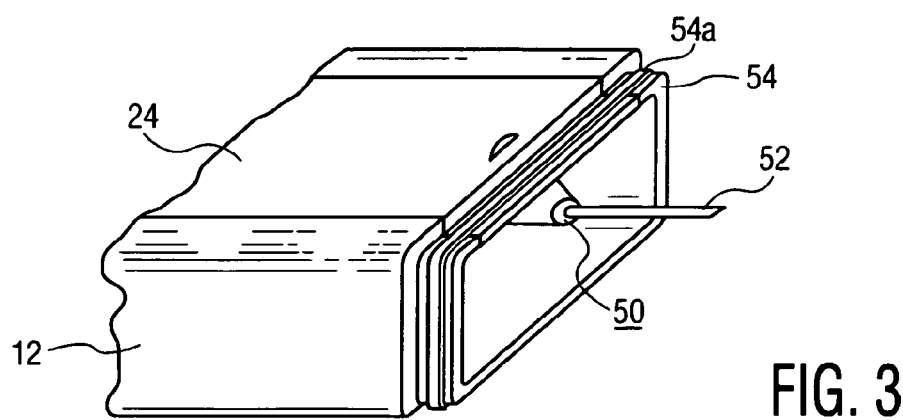
FIG. 3 partially depicts in schematic fashion an insulin injection mechanism with a hypodermic needle that forms a part of the insulin pen and blood glucose monitor unit shown in FIG. 1.

FIG. 3 shows an exemplary embodiment of an insulin injection mechanism 50. The insulin injection mechanism includes a cap 14 as shown in FIGS. 1A and 1B to protect the hypodermic needle 52 from damage and to prevent inadvertent needle sticks. The cap is not shown in FIG. 3. As with the cap 32, the cap 14 of the insulin injection mechanism fits snugly onto the end of the housing in a manner similar to that used for the cap 32. That is, the housing 12 presents an external shoulder 54 with a circumferential ridge 54a. The external shoulder 54 fits into an internal shoulder on the cap 14 (not shown) to hold the cap 14 in place on the housing in a manner similar to that described above for the cap 32. The outside peripheral surfaces of the cap 14 and housing 12 are flush in order to maintain the unitary appearance of the unit 10 when the cap is in place on the housing. U.S. Pat. No. 5,728,074 mentioned above describes various ways of implementing an insulin injection mechanism. Any of those mechanisms, or variations thereof, can be used in the unit 10 of the present invention, and those portions of U.S. Pat. No. 5,728,074 describing insulin injection mechanisms are incorporated by reference as if set out in full herein. Many of the other patents discussed above also describe insulin injection mechanisms, and any of those mechanisms can be used in the unit 10 as well. If the user has to gain access to the interior components of the insulin injection mechanism for any reason, such as to replace a cartridge containing plural insulin doses, the cover 24 can be removed to provide such access.

Referring back to FIG. 1A, the side of the housing 12 opposite the side having the insulin injection mechanism access opening 24 and the battery compartment 26, can be considered the front of the unit. It has a user interface that comprises two manual input devices 102 and 108 and an LCD display 200. The manual input device 102 is a circular touch-activated device in which each of four regions separated by 90° provide an input signal when touched by a user. Touching a center region provides a SELECT command. The input device 108 acts a mode switch by which the user can set a mode of operation of the device by moving an image of a slider to the right or left. A more detailed description concerning the layout and operation of the input devices is provided below in connection with FIG. 5. These devices, together with the LCD display 200, enable operation of the device as described in detail below. These input devices can take alternate forms, such as mechanical switches that close respective electrical circuits when pressed. They can also have different configurations, and be located on the unit 10 in locations other than as depicted in the accompanying drawings. In its broadest aspects, the invention includes all manner of input devices capable of providing the desired control functions. The LCD display 200 is capable of displaying different screens, depending on the input from the manual input devices or the unit's controlling software. The LCD display can be backlit with different colors for purposes described in more detail below. Those skilled in the art will recognize that other types of display devices can be used within the scope of the invention. A more complete description of the user interface is deferred until the discussion further below of the operation of the unit 10 and its improved manner of enabling diabetes patients to more easily and safely manage their symptoms.

Figure 4:
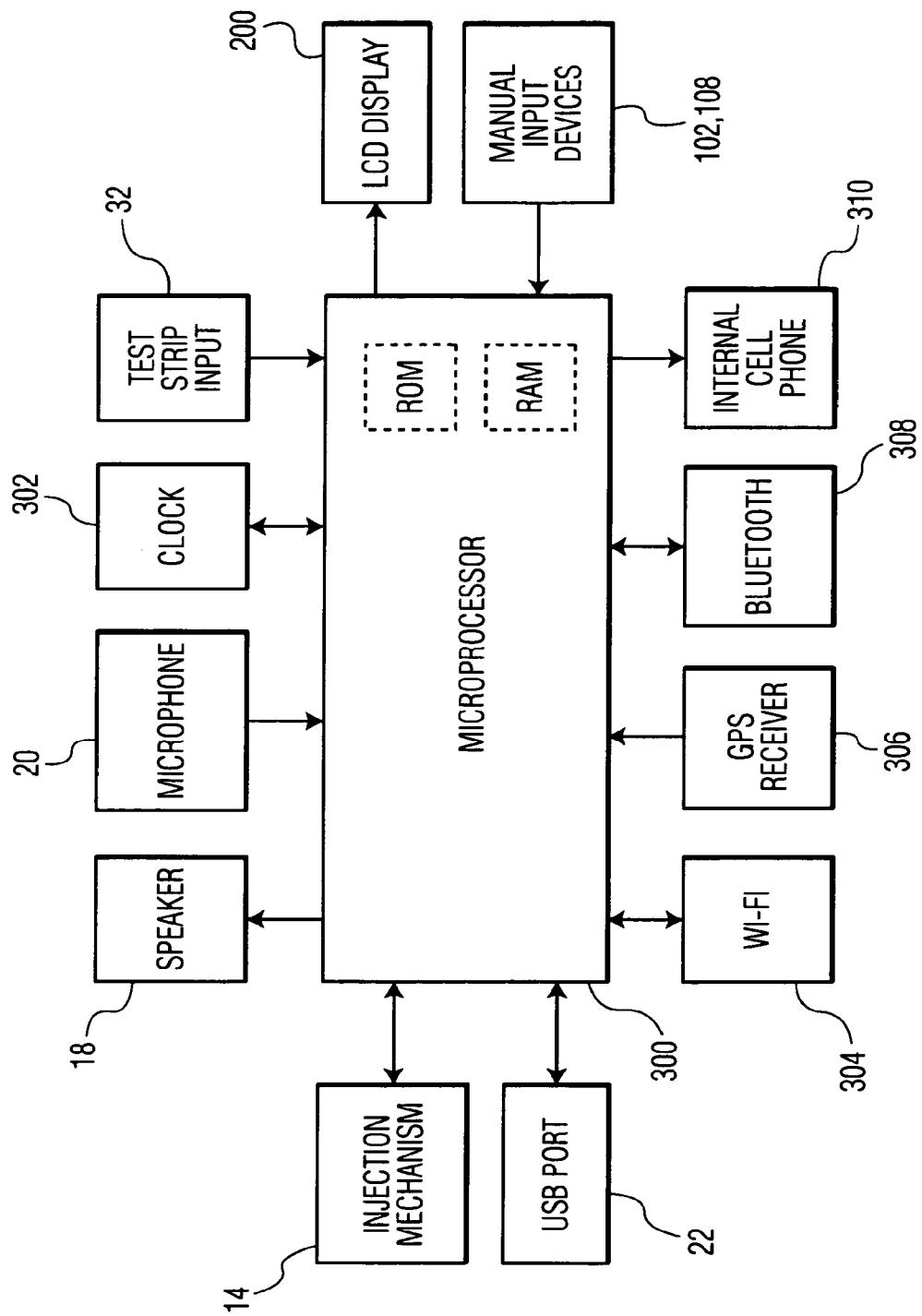
FIG. 4 is a simplified block diagram showing the system components for an blood glucose monitor and insulin pen unit according to one embodiment of the present invention such as that shown in FIGS. 1 to 3.

FIG. 4 shows the system components for providing the operating functions of the unit in accordance with particular embodiments of the invention. The unit is under the overall control of a microprocessor 300 that incorporates a read-only memory ROM storing an operating system and executable programs that use algorithms and data provided to the unit to determine insulin dosages and other parameters useful in managing the patient's symptoms, and that control the operation of the various other components of the system described just below. The microprocessor 300 also includes a random access working memory RAM to enable the microprocessor to execute programs stored in the ROM. A clock 302 in the housing 12 is under the control of the microprocessor 300. The clock provides time and date information to the microprocessor for display on the LCD display, as discussed below. The microprocessor 300 can also condition the clock 302 to function as a timer for providing elapsed time data to the microprocessor for purposes also discussed below.

In the present embodiment the unit 10 further includes Wi-Fi circuitry 304 in the housing 12 and under the control of the microprocessor 302. The Wi-Fi circuitry can communicate with remote locations via wireless connection to the Internet if the unit 10 is sufficiently close to a Wi-Fi router. This enables information to be sent and received by the unit wirelessly at very high speeds. The unit 10 further includes a GPS (Global Positioning System) receiver 306 that receives signals from a GPS satellite to indicate the global longitude and latitude of the unit. The unit can also include Bluetooth circuitry 308 for wireless connection to a peripheral device such as a user's cellular telephone or personal digital assistant (not shown). Finally, the present embodiment also includes an internal cellular telephone 310 for dialing remote locations under the control of the microprocessor 300. The cellular telephone can further include so-called 3G or 4G circuitry for connection to the Internet when connection to a Wi-Fi router connection cannot be made. The functions and purposes of these components are discussed below in connection with the operation of the unit 10.

Figure 5:
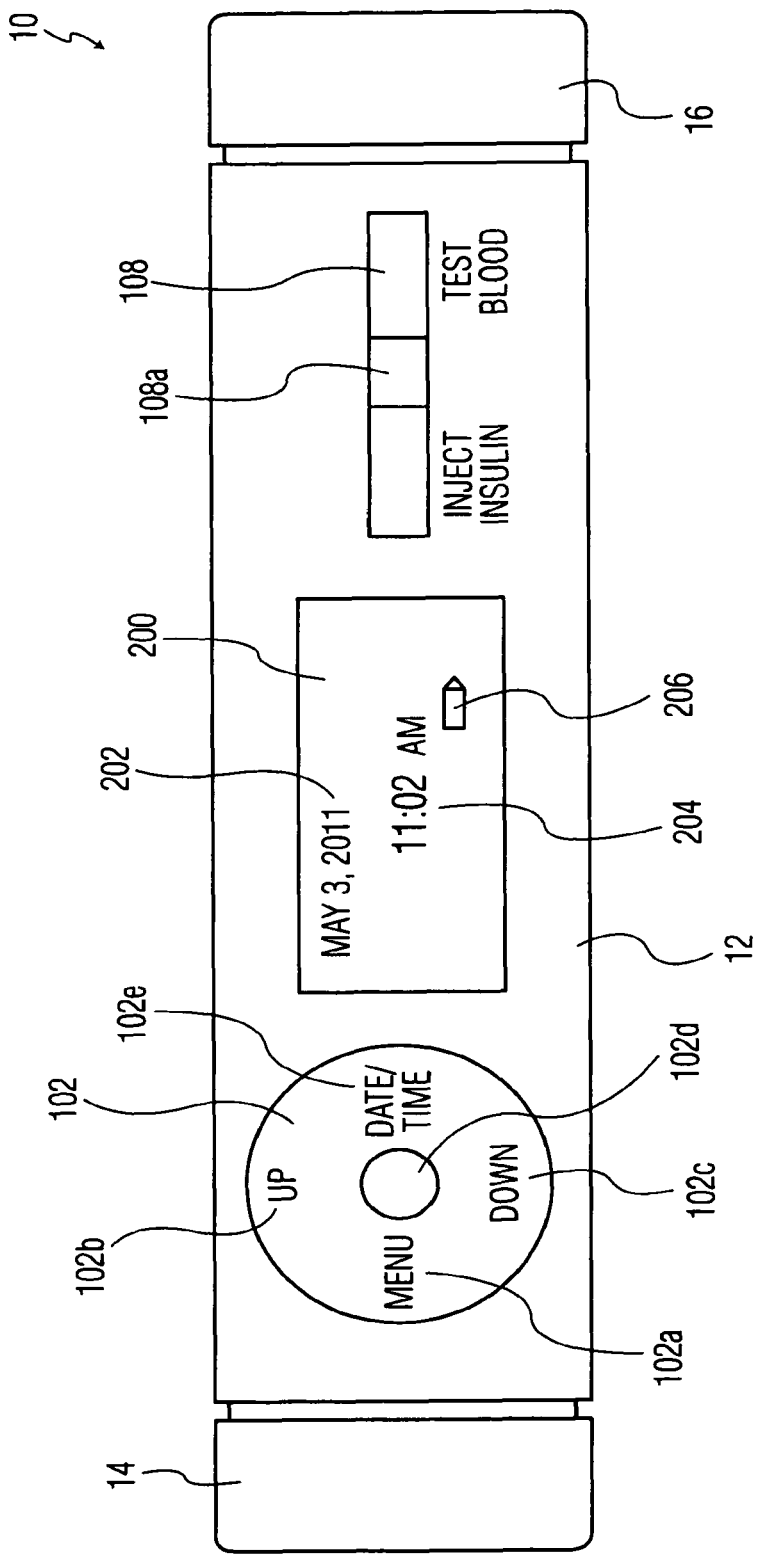
FIG. 5 illustrates an embodiment of a user interface with an LCD display and manual input devices incorporated into the unit shown in FIG. 1.

FIG. 5 is a detailed view of the front of the unit 10, showing the layout of the manual input devices 102 and 108 and the LCD display 200. The four regions spaced at 90° around the periphery of the touch-activated input device 102 provide separate input functions. A MENU "button" 102a at a nine o'clock position on the circular device 102 causes a menu of control options to be displayed on the LCD display 200. An UP "button" 102b at twelve o'clock and a DOWN "button" 102c at six o'clock on the device 102 enable the user to scroll through and highlight menu choices shown on the LCD display. The center of the device 102 comprises a touch-activated SELECT "button" 102d that selects the highlighted choice. The region at three o'clock is a DATE/TIME "button" 102e that causes the LCD display 200 to indicate the date 202 and the time of day 204, as shown in FIG. 5. The LCD display also includes a battery status indicator 206 that indicates in a conventional manner the amount of battery life remaining. The unit defaults to the date/time display in the absence of other inputs to the device 102. The mode switch 108 has an image of a slider 108a that acts as a switch "button." Unit software maintains the slider image in a default position midway between the right and left ends of the image display that comprises the input device 108. A user slides the button to the right (as seen in FIG. 5) to activate the glucose monitoring system 16 and to the left to activate the insulin injection mechanism 50. The unit may also include a separate button (not shown) that "locks" the devices 102 and 108 so that they cannot be inadvertently actuated. The use of the input devices and the LCD display to operate the unit is discussed in more detail as part of the following explanation of how one embodiment of the unit is typically used to manage the symptoms of a diabetes patient.

Initialization of the Unit

To perform the tasks described herein, the unit 10 requires initial set up by inputting data from the patient's healthcare provider. In its most basic form, this involves loading data into the ROM in the device microprocessor 300 that will enable the programs stored therein to calculate insulin dosages and specify treatment regimens based on the user-patient's tested glucose level. This data can be input using a portable USB drive (not shown) on which the necessary information has been stored by the healthcare provider and which is then plugged into the USB port 22, or by sending the information to the unit over the Internet via a receiver included in the Wi-Fi circuitry 304 or the cellular telephone circuitry 310 included in the unit.

The necessary data is loaded into the unit's ROM by the healthcare provider so that it is available when the patient uses the unit. The data would typically include information such as insulin dosages and types and amounts of glucose-producing substances to be consumed based on tested blood glucose levels, and any other data or parameters required by the algorithms in the ROM used by the device to determine a given insulin dosage or amount and type of glucose-producing substance to be ingested appropriate to a patient's tested blood glucose level. The exact nature of this data does not form a part of the present invention, and literature such as the references already discussed above illustrate the type of data that can be used in this regard. The data loaded into the unit also includes at least four blood glucose levels for the particular patient-user:

L1: Threshold level for severe hypoglycemia
L2: Threshold level for mild hypoglycemia
L3: Threshold level for mild hyperglycemia
L4: Threshold level for severe hyperglycemia The description that follows of a testing/treatment/emergency notification process using the unit of the present invention assumes that a treatment protocol with the necessary information appropriate to the particular patient using the unit has been stored in the unit ROM.

One way of uploading the necessary data to the unit uses the input device 102 and the LCD display 200 under the direction of the microprocessor 300. For example, in one possible embodiment the MENU region 102a of the input device 102 would be touched when data was to be uploaded to the unit 10. The microprocessor could be programmed to prompt insertion of a USB drive into the USB port 22 if that had not already been done, and then to cause the LCD to display a menu of prompts that a user can scroll through using the UP and DOWN buttons 102b and 102c to highlight displayed prompts in order. For example, a menu could include a number of options, one of which is "INPUT DATA." The UP and DOWN buttons would enable the user to highlight that option and activation of the SELECT button 102d would cause the data to be uploaded into the unit. Any other prompt menus necessary at various times during a data upload could be displayed and chosen in the same fashion.

Another menu item could permit the user to choose the language in which the unit will display messages and provide voice prompts during use of the unit for blood glucose monitoring and insulin injection. For example, one of the menu choices could be LANGUAGE, and once that menu item is highlighted by scrolling to it using the UP or DOWN button, touching the SELECT region 102d causes the LCD display to list the available languages. Again, the UP or DOWN button is used to scroll to and highlight the desired language choice, and the SELECT region 102d is touched to select the highlighted language choice. Typically, the default language will be English, and messages and voice prompts will be in English unless changed.

Using the Unit for Blood Glucose Testing and Insulin Injection

Figure 6A:
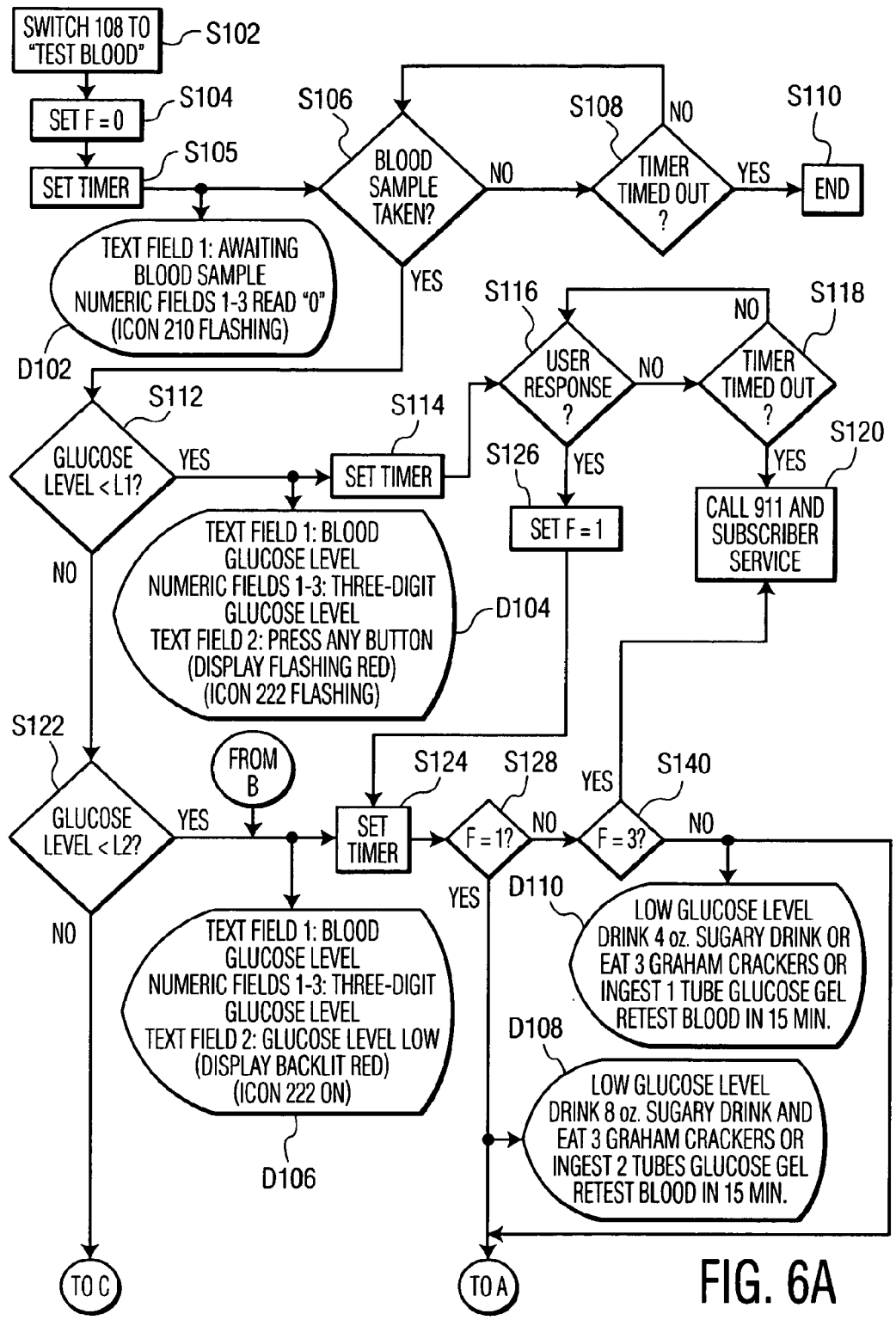
FIGS. 6A, 6B and 6C, is a flowchart depicting the steps in a blood glucose test and insulin injection cycle according to an embodiment of the present invention.
Figure 6B:
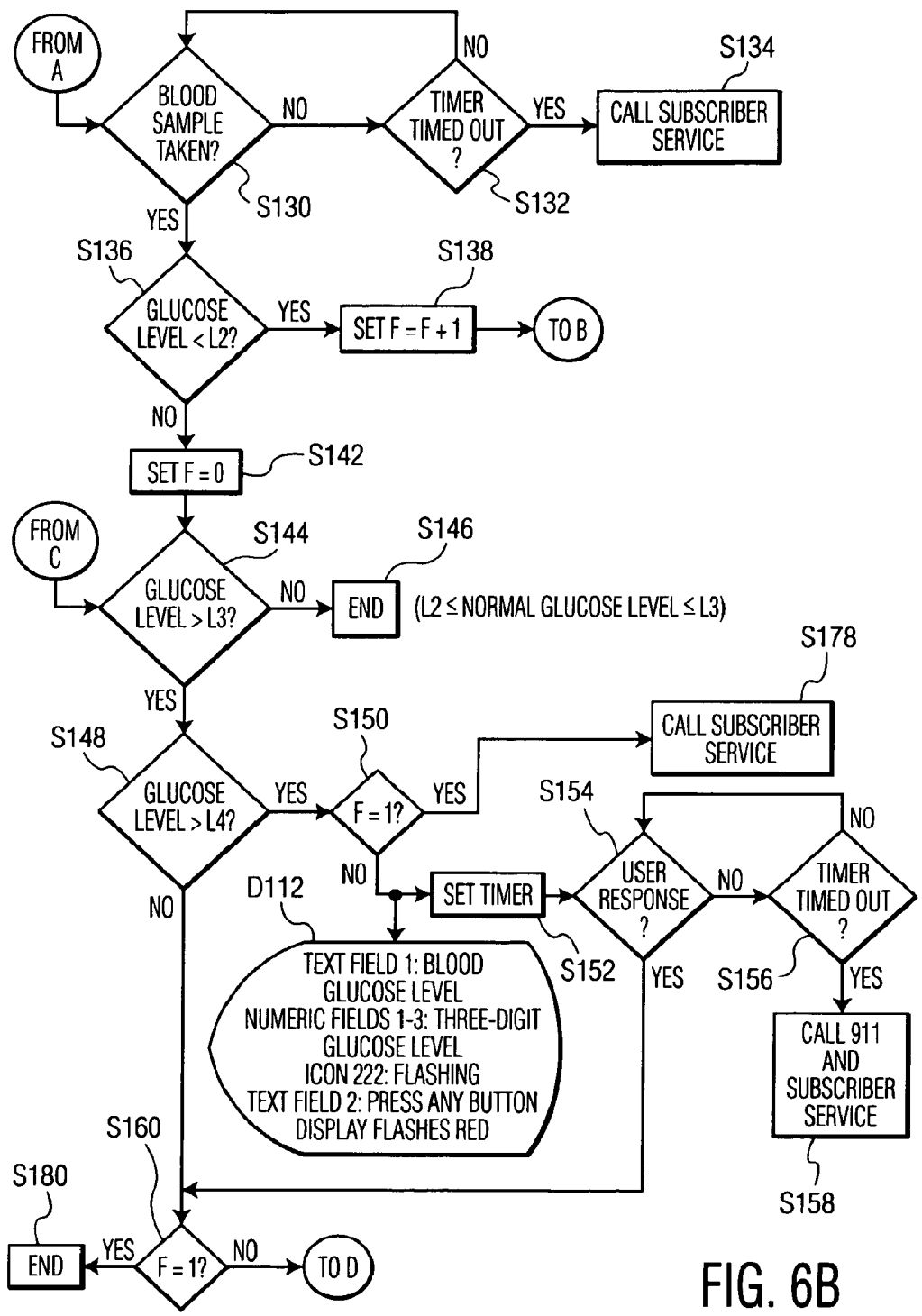
Figure 6C:
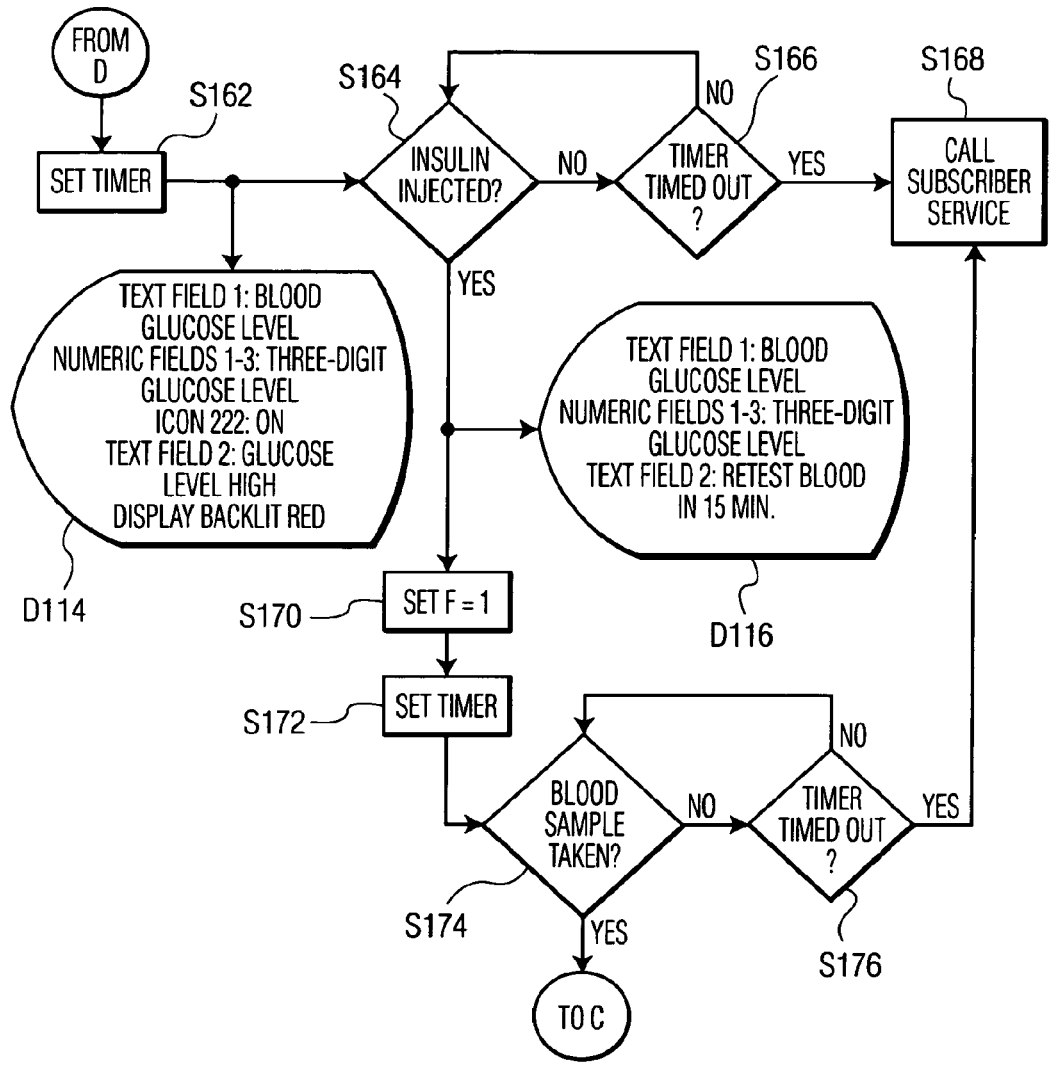

FIG. 6 is a flowchart depicting the manner in which the unit 10 operates to perform a testing/treatment/emergency notification process according to one embodiment of the invention. It will be understood that the steps shown in the flowchart of FIG. 6 are under the control of application software stored in the ROM in the microprocessor 300 and executed by the microprocessor 300 in a conventional fashion. Any suitable programming language or technique can be utilized to carry out the steps depicted in FIG. 6 or their equivalents, and the invention is not limited to any particular software configuration.

A patient initiates a blood glucose test in step S102 by sliding the mode switch button image 108a to the right as seen in FIG. 5 to the "TEST BLOOD" mode of operation. This sets a flag F to "0" in step S104 and sets a timer in step S105 to count down a sufficient time for the user to perform a blood glucose test as described below in connection with step S106. A suitable time period is preferably about five minutes, but can be any appropriate time period between, say, three minutes and 10 minutes.

Figure 7:
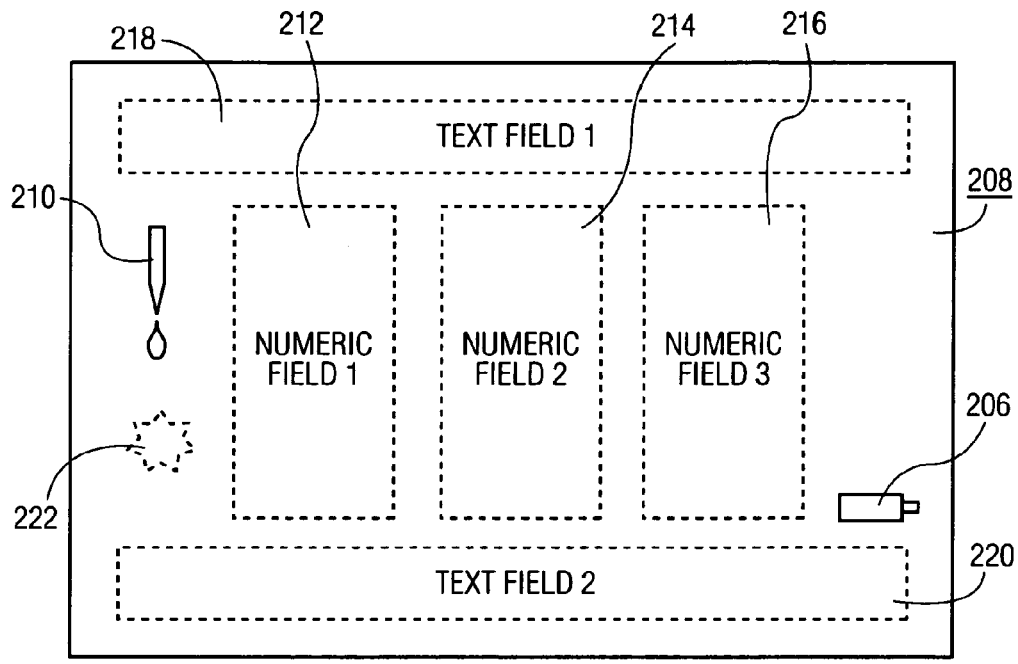
FIG. 7 illustrates a display mode of the LCD display shown in FIG. 5 in which it can display numeric fields indicating a blood glucose level, insulin dosage, and other information.

At the same time, the microprocessor 300 causes the LCD display 200 to display the screen 208 shown in FIG. 7. This screen includes the battery status indicator 206, so that the user always has a visual indication of how much charge remains in the unit's batteries. It further includes an icon 210 that indicates the status of the blood testing procedure, three numeric fields 212, 214 and 216, and two text fields 218 and 220. As seen in display status box D102, the blood test status icon 210 is flashing and the first text field 218 contains the message "AWAITING BLOOD SAMPLE." The numeric fields all display the numeral "0" and the second text field 220 is blank. (The dotted lines denoting the numeric and text fields in FIG. 7 indicate the positions of the fields on the display; the dotted lines are not part of the display.) A star-shaped alarm icon 222, described in more detail below, is not visible in the display indicated by the display status box D102. The microprocessor 300 can be further programmed to provide a voice message to the speaker 18 that repeats the message displayed in the first text field 218. The capacity to echo a text message with a voice prompt can be an important feature because impaired vision or even blindness can be a side effect of diabetes.

The unit then waits at step S106 for the patient to take a blood sample and initiate a blood glucose level test. To take a blood sample, the patient removes the cover 32 from the blood glucose monitoring system 16 (see FIG. 2), retrieves a lancet 30 from inside the cap 32, affixes it to the cap, and pierces a finger using the lancet 30. As described above in connection with FIG. 2, the patient places a blood sample on the test strip 33, which the user has extended from a cartridge within the unit housing 12. When the blood sample reaches the glucose sensing components within the unit 10, the icon 210 stops flashing and is lit continuously, while the first text field 218 contains the message "TESTING GLUCOSE LEVEL" (not shown in FIG. 6). During the time elapsed after the timer is set in step S105, the microprocessor continuously checks to see if the timer has timed out. This is represented by the loop including steps S106 and S108. As before, the microprocessor 300 can be programmed to provide a voice message to the speaker 18 that repeats the message displayed in the first text field 218. If the timer times out before the unit detects the presence of a blood sample, the process terminates, as shown at step S110. This causes the unit to go into a "sleep" mode to save battery life. Any suitable manner of "waking" the device can be used. For example, in the sleep mode the LCD display would be off, but touching either input device 102 or 108 could cause the display of a message that touching the DATE/TIME region 102e will activate the unit.

Blood Test Results Indicate Hypoglycemia

If the microprocessor detects a blood sample before the timer times out, the process proceeds to step S112, which initiates an important aspect of the invention. As noted above, the microprocessor ROM stores data relating to normal blood glucose levels particular to the patient using the unit, as well as certain predetermined levels that indicate different blood glucose readings that the patient can safely tolerate. In step S112 the microprocessor determines if the tested blood glucose level is below the critical predetermined level L1 that indicates severe hypoglycemia and could result in the imminent onset of diabetic coma in this particular patient. If so, another time period is set in step S114. At the same time, the LCD display 200 displays the blood glucose level in the numeric fields 212, 214 and 216, and the first text field 218 now reads "BLOOD GLUCOSE LEVEL." The display can optionally indicate the units in which the blood glucose level is displayed, but in a preferred embodiment the level is expressed in the standard units of mg/dL and no indication of the units is necessary. If the blood glucose level is less than L1, the LCD display is back lit in flashing red, the star-shaped alarm icon 222 begins flashing red to indicate a severe hypoglycemic condition, and the second text field 220 is changed to read "PRESS ANY BUTTON," as seen in display status box D104. The microprocessor also sends to the speaker 18 an audible prompt such as, "To terminate alarm condition press any button on the unit or say 'OK.'"

During the time elapsed after the timer is set in step S114, the microprocessor continuously checks to see if the timer has timed out. This is represented by the loop including steps S116 and S118. A suitable time period is about 10 seconds, and is preferably not more than one minute. The purpose of this time period is to give the user an opportunity to respond in a manner that indicates that the user has not become disoriented, or even entered a diabetic coma, because of the indicated severe hypoglycemia detected by the blood test. If the user-patient presses anyplace on the input device 102, or the microphone 22 picks up an audible signal that voice recognition software in the microprocessor recognizes as "OK," before this time period expires, the microprocessor proceeds to the next portion of the process, discussed further below.

However, if the timer times out before the patient responds, the unit 10 responds at step S120 with an automatic call using the unit's internal cellular telephone 310 to call a public emergency service provider by dialing 911 and to call a presubscribed emergency service such as the Alert One® medical alert service provided by Alert One Services, Inc., of Williamsport, Pa. The unit sends a prerecorded message to 911 and to the subscriber service that identifies the caller, states that he or she may be in a diabetic coma, and includes information on the unit's location provided by the GPS receiver 306. The unit's ROM can include software and a database for converting the unit's global coordinates provided by the GPS receiver 306 into usable location information, such as a street address, but the capability of converting the coordinates into location information can also be at the call reception location, or via a handheld device such as an Apple iPhone® with which the unit communicates via its Bluetooth circuitry 308. In the latter case, the call to the emergency service provider can be made by the external device, as well. Communicating with both 911 and a private subscriber service ensures that the patient will obtain the medical attention necessary because of his or her severe hypoglycemia.

The automatic notification of 911 and/or an emergency subscriber service is an important aspect of the invention. One of the objects of the present invention is to enable a diabetic patient to maintain a lifestyle that is as normal as possible, while still managing the symptoms of his or her diabetes. To do that, the user must have a level of confidence that a self-monitoring device can reduce the chances for negative outcomes if his or her symptoms should become so severe that they present a serious, or even life-threatening, situation. By providing for automatic notification of an emergency service provider ("911" and/or a subscriber service) as discussed herein, the unit 10 gives the user-patient confidence that symptoms that are so severe that he or she may not even be able to recognize their existence, will automatically engender an emergency response and immediate emergency treatment or other appropriate action. The other instances discussed below in which the unit 10 performs automatic emergency notifications achieve the same effect.

Returning to step S112, if the tested blood glucose level is higher than the level L1, the process proceeds to step S122, where the level is now compared to the predetermined minimum level L2 for the particular patient for whom the unit has been set up. A blood glucose level below L2 indicates that the patient is mildly hypoglycemic and needs to increase his or her blood glucose by ingesting a suitable blood glucose producing substance. To that end, the microprocessor sets the LCD display 200 as indicated in display status box D106, with the LCD steadily back lit in a different color, such as red, to indicate a hypoglycemic condition, with the star-shaped alarm icon 222 illuminated, and with the message "GLUCOSE LEVEL LOW" in the second text field 220. At the same time, the microprocessor sets another time period in step S124, for a purpose described further below. As indicated in the figure, the process also proceeds to step S124, after setting the flag F=1 in step S126, when the unit detects a user response from a severely hypoglycemic patient (step S116).

Figure 8:
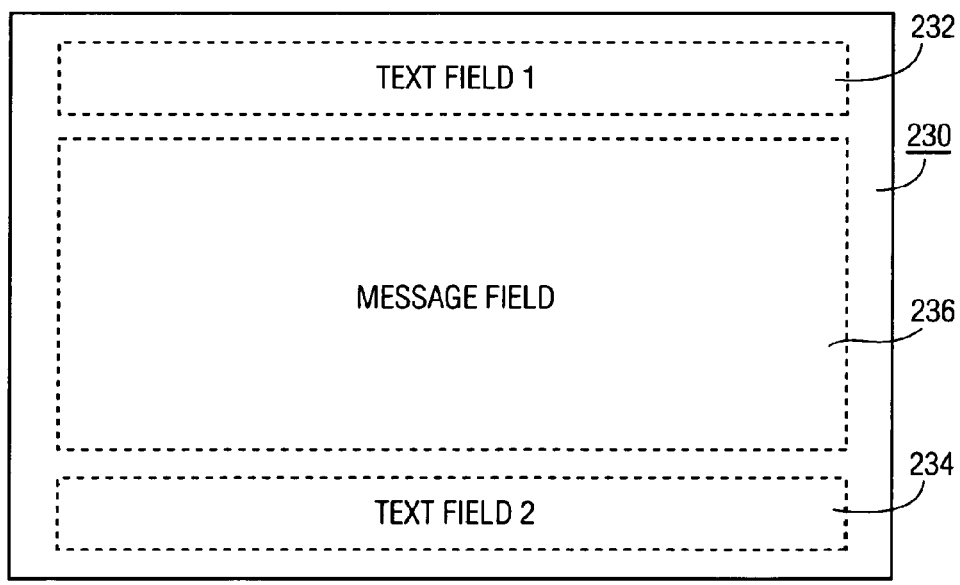
FIG. 8 illustrates a display mode of the LCD display shown in FIG. 5 in which it can display messages to the user.

Next, the process checks the status of the flag F in step S128. If F=1, indicating a severe hypoglycemic condition, the LCD display 200 changes to the mode shown in FIG. 8 to display a treatment regimen to the user. This screen 230 includes a first text field 232 and a second text field 234, corresponding to the first and second text fields of screen 208 shown in FIG. 7. The numeric fields of screen 208 are replaced by a message field 236, which is capable of displaying treatment instructions to the patient-user. (As with screen 208, the dotted lines in screen 230 shown in FIG. 8 denoting the text and message fields indicate the positions of the fields and are not part of the display.) Text field 232 now reads "LOW GLUCOSE LEVEL," indicating that the patient needs to ingest a carbohydrate-containing substance. In accordance with known treatment protocols, the type of substance will generally be in the nature of a sugary drink, such as a commercially available fruit juice, a solid food containing sugar and/or other carbohydrates, or a glucose gel available for the express use of diabetic patients. The amount of the substance will reflect that the patient's blood glucose level is at a dangerously low level less than L1 (see steps S112 and S126). According to one standard protocol, the unit software causes the message field 236 to display treatment regimen instructions such as shown in display status box D108:

Drink 8 oz. sugary drink AND
    Eat 3 graham crackers, OR
    Ingest 2 tubes glucose gel.

In addition, the second text field 234 reads "RETEST BLOOD IN 15 MIN." This provides sufficient time for the patient's blood glucose level to respond to the ingestion of the prescribed substance(s). It will be understood by those skilled in the art that the particular substances listed here are representative and may be other substances within the scope of the invention. In addition, the 15-minute waiting time is also representative, and it too can be other time periods if deemed appropriate for a given patient. Indeed, the substances to be consumed and the waiting period between blood tests can be tailored to the individual patient-user of the unit and stored in the unit ROM for display as discussed here.

The time period set in step S124 allows for the waiting period just discussed, that is, 15 minutes in the present embodiment of the invention, plus an interval that will allow sufficient time to take the next blood test. In an alternate embodiment, the unit can first set a 15-minute time period and then prompt the user to perform the next blood test by displaying a screen similar to that shown in display status box D102 and/or generating an audible signal such as a repeating beeping sound. Then, another time period will be set as in step S105 with a time period such as five minutes in which the user must perform the blood test. In any case, the microprocessor continuously checks to see if the timer has timed out, as represented by the loop including steps S130 and S132.

If the patient fails to take another blood sample within the time allotted, the unit 10 responds at step S134 with an automatic call using the unit's internal cellular telephone 310 to the subscriber service such as the Alert One® medical alert service discussed above. The call identifies the caller, states that he or she is not responding as required by his or her treatment protocol, and includes a prerecorded message that includes information on the unit's location provided by the GPS receiver 306. The subscriber service will then call the user to make a judgment as to whether or not emergency service is required. A call to 911 is not made at this time since it is unlikely that the user is in imminent danger of entering a diabetic coma considering the amount of blood glucose producing substances that have just been ingested.

In another alternate embodiment, the microprocessor can be programmed to await the user's confirmation that the blood sugar producing substances have been ingested as instructed. That is, if the protocol incorporates a first 15-minute period to allow for the ingestion of the substances as directed by the unit, the user could be required by a message on the LCD display 200 and/or an audible prompt to confirm that the specified substances were consumed before the second time period waiting for the next blood test is set. If the user does not respond as directed, the process would go to step S120. This embodiment would account for a severely hypoglycemic patient who was able to respond in step S116, but nevertheless did not respond in time to the ingestion of the directed substances to prevent disorientation or coma.

If the unit receives the results of the second blood test before the timer times out, the process advances to step S136, where the glucose level is again compared to L2. If the patient is still hypoglycemic (blood glucose level<L2), the process first proceeds to step S138 where it increments the status of the flag by 1, so that F=2, and then returns to the point where the LCD display 200 exhibits display status box D106, with the numeric fields 212, 214 and 216 now displaying the current glucose level. Step S124 sets the same time period a second time and the process proceeds to step S128. Since F=2 (that is, F≠1), step S128 directs the process to step S140, where it is determined if F=3.

It will be appreciated that if the first blood test taken in step S106 resulted in a blood glucose level between L1 and L2, indicating milder hypoglycemia, the process will also reach step S140, since in that event step S128 will detect that F=0 (that is, F≠1). Step S140 then detects F≠3, meaning that the LCD display 200 again changes to the mode depicted in FIG. 8. According to the treatment protocol represented by the present embodiment, the unit's software causes the message field 236 to display the following treatment instruction, as shown in display status box D110:

Drink 4 oz. sugary drink, OR
 Eat 3 graham crackers, OR
  Ingest 1 tube glucose gel In addition, the second text field 234 reads "RETEST BLOOD IN 15 MIN." This provides sufficient time for the patient's blood glucose level to respond to the substance(s) ingested to raise his or her glucose levels. The unit will now wait for the results of a second blood test, as effected by the loop comprising steps S130 and S132. If a blood test is not taken before the timer times out, the process proceeds to step S134, described above.

Severely Hypoglycemic Patient after the Second Blood Test.

If the second blood test for a severely hypoglycemic patient still indicates a hypoglycemic condition, the amount of the substances that will raise the user's blood glucose levels is reduced from the amount that was ingested after the first blood test. This is effected by the status of the flag F, which was set at F=2 after the second blood test. Step S128 now detects that F≠1 and advances the process to step S140, which detects that F≠3. Consequently, the LCD display issues the instruction shown in display status box D110, instructing the patient to perform a third blood test, and then advances to step S130. If the third blood test indicates that the patient's glucose level is still less than L2, step S138 sets the flag status F=3 (F=2+1), and returns the process to the point where the LCD display 200 exhibits display status box D106, with the numeric fields 212, 214 and 216 displaying the current glucose level. Step S124 sets the same time period again and the process proceeds to step S128. Now, F=3 (that is, F≠1), step S128 directs the process to step S140, which detects that F=3. This causes the unit to proceed to step S120, which is described above. In other words, the protocol of the present embodiment assumes that the failure of the patient's severe hypoglycemia to respond to the ingestion of large amounts of glucose-producing substances indicates a possible emergency condition and warrants a call to 911.

Mildly Hypoglycemic Patient after the Second Blood Test.

If the second blood test for a more mildly hypoglycemic patient still indicates a hypoglycemic condition, the amount of the substances that will raise the user's blood glucose levels is increased from the amount that was ingested after the first blood test. This is effected by the status of the flag F, which step S138 set at F=1 after the second blood test. Step S128 now detects that F=1 and the LCD display 200 displays the instruction in display status box D108 and waits for the results of a third blood test, as effected by the loop comprising steps S130 and S132. In other words, the protocol of the present embodiment increases the amount of blood glucose producing substances to be ingested by the patient because of his or her failure to adequately respond to the ingestion of a smaller amount per the instruction in display status box DUO. Assuming a third blood test is taken within the time allotted (steps S130 and S132), the process then determines if the user's blood glucose level is now at least L2. (If a third blood test is not taken before the timer times out, the process proceeds to step S134, described above.)

If the third blood test indicates that the patient's glucose level is still less than L2, step S138 sets the flag status F=2 (F=1+1). The process returns to the point where the LCD display 200 exhibits display status box D106, with the numeric fields 212, 214 and 216 displaying the current glucose level.

The patient now can ingest additional blood glucose containing substance(s) and take a fourth blood test, since step S140 will detect that the flag status F≠3. However, the patient may decide based on personal experience that the glucose level already achieved (as displayed in display status box D106) is acceptable, and elect not to take a fourth blood test. In that event, the timer times out, the unit calls the subscriber service (step S134), and the patient can confirm to the caller that he or she has an acceptable glucose level and does not need assistance. However, if the user elects to take a fourth blood test, step S136 again determines if the tested glucose level is still below L2. If so, step S138 sets the flag status F=3 (F=2+1), and when the process reaches step S140, it will detect that flag status and proceed to step S120, as discussed above. In other words, this particular protocol assumes that the patient requires emergency assistance since the repeated ingestion of blood glucose producing substances has not remedied a detected hypoglycemic condition.

If at any time, step S136 detects a blood glucose level that is not less than L2, the process proceeds to step S142, where the flag status F is set to F=0, and then proceeds to step S144, which determines if the user's blood glucose level is not above L3, thus indicating that is in the normal range between L2 and L3. If so, the process terminates, as indicated in step S146 (similar to step S110). If step S144 indicates that the user's blood glucose level exceeds L3, it indicates a hyperglycemic condition, possibly requiring the administration of an insulin injection. In addition, if the first blood test (step S106) indicates a blood glucose level that exceeds L2, the process also proceeds to step S144 (see steps S112 and S122). Step S146 can be accompanied by a message on the LCD display 200 indicating that the user's blood glucose level is normal, with the background of the display lit in steady or flashing green, to provide an immediately recognizable indication that the user's glucose level is acceptable.

Blood Test Results Indicate Hyperglycemia

If step S144 indicates that the user's blood glucose level is above L3, the next step S148 determines if the level is above L4, thus indicating more severe hyperglycemia. If so, the process proceeds to step S150 to check the status of the flag F. Since the flag F was set F=0 (step S104 or step S142), the process proceeds to step S152. At the same time, the LCD display 200 displays the blood glucose level in the numeric fields 212, 214 and 216, and the first text field 218 now reads "BLOOD GLUCOSE LEVEL." The LCD display is back lit in flashing red, the star-shaped alarm icon 222 begins flashing red to indicate a severe hyperglycemic condition, and the second text field 220 is changed to read "PRESS ANY BUTTON," as seen in display status box D112. The microprocessor also sends to the speaker 18 an audible prompt such as "To terminate alarm condition press any button on the unit or say 'OK.'"

During the time elapsed after the timer is set in step S152, the microprocessor continuously checks to see if the timer has timed out. This is represented by the loop including steps S154 and S156. A suitable time period is preferably about 10 seconds, and is preferably not more than one minute. The purpose of this time period is to give the user an opportunity to respond in a manner that indicates that the user has not become disoriented because of the indicated severe hyperglycemia detected by the blood test. If the user-patient presses any place on the input device 102, or the microphone 22 picks up an audible signal that voice recognition software in the microprocessor recognizes as "OK," before the time period expires, the microprocessor proceeds to the next portion of the process, which is discussed further below.

However, if the timer times out before the patient responds, the unit 10 responds at step S158 with an automatic call using the unit's internal cellular telephone 310 to 911 and to the subscriber service. These calls correspond to the calls described above in connection with step S120. That is, the unit sends a prerecorded message to 911 and to the subscriber service that identifies the caller, states that he or she is severely hyperglycemic, and includes information on the unit's location provided by the GPS receiver 306, as discussed above.

If the user has responded before the time period set in step S152 expires, the process proceeds to step S160, where the status of the flag is checked to determine if F=1. The process also proceeds to step S160 if the user's blood glucose level is not greater than L4 as determined in step S148. In either event, since F=0 (F≠1), the process proceeds to step S162 where a time period is set. At the same time, the unit sets the LCD display 200 as shown in display status box D114, with the LCD back lit in red to indicate an abnormal condition (in this case, hyperglycemia), with the star-shaped alarm icon 222 illuminated, and with the message "GLUCOSE LEVEL HIGH" in the second text field 220. The unit then awaits for the user to administer an insulin injection within the time period set in step S162. This is indicated by the loop including steps S164 and S166, during which the unit continuously checks to see if an insulin injection has been administered using the unit's insulin injection mechanism described above. The display screen 230 in FIG. 8 can be used at this point to indicate that the prescribed treatment regimen is an insulin injection (not shown).

If the time period times out before an insulin injection is detected, the unit places a call to the subscriber service in step S168. This call is similar in nature to the call placed in step S158. That is, since the patient responded if severe hyperglycemia was detected in step S148, or alternatively the patient is only mildly hyperglycemic as per step S144, the protocol of the present embodiment assumes that a life-threatening situation is not present. Accordingly, the subscriber service will typically telephone the user to determine if he or she is fully aware of the condition and has voluntarily chosen not to take action. In other words, this protocol judges that a call to 911 for immediate emergency assistance is not warranted.

Administering an Insulin Injection

To activate the insulin injection mechanism 50, the patient moves the mode switch slider image 108a on the unit 10 to the left as seen in FIG. 5 to the "INJECT INSULIN" mode of operation. The microprocessor ROM contains an algorithm that uses the patient's blood glucose reading, the time elapsed since the previous insulin injection, and other pertinent information or parameters, to calculate the proper insulin dose. When the results of a blood glucose test are available (see above), and the mode switch button 108a is in the INJECT INSULIN position, the insulin dose calculated by the algorithm is displayed (not shown in the figures) in the numeric fields 232, 234 and 236 depicted in FIG. 7 in standard dose units of 0.01 cc each.

The UP and DOWN buttons (see FIG. 5) can be used by the patient to change the amount of insulin to be injected. However, after the unit sets the dosage amount an attempt by the user to change it with the UP or DOWN button will trigger the unit's "dose lock" feature, which causes the LCD display to display a prompt, such as "ARE YOU SURE YOU WANT TO CHANGE DOSAGE?" (not shown). In order to effect any change in the dosage calculated by the unit's algorithm, the user must touch or press the SELECT button 102d to override the dose lock feature. This dose lock feature helps to prevent injection of inappropriate amounts of insulin by requiring the patient to confirm that he or she wants to override the dosage calculated by the unit. The healthcare community has recently begun to focus more strongly on the potential for medical errors in many environments to have severe adverse effects on patients. The unit 10's dose lock feature provides an effective way to prevent the occurrence of serious insulin dosage errors in the environment of diabetes patients' self-monitoring and self-treatment of their symptoms.

Once the dosage amount has been set (either automatically by the unit's algorithm or as manually adjusted by the patient after overriding the dose lock), the patient presses the SELECT button 102d, which changes the display so that the first and third numeric fields 232 and 236 are blank, the second numeric field 234 displays a "5," the first text field 238 displays the message "AWAITING INJECTION," and the second text field 240 contains the message "INSERT NEEDLE" (not shown in the figures). The microprocessor 300 can be programmed to provide a voice message to the speaker 18 that repeats the message displayed in the second text field to provide a voice prompt to administer the injection.

If the patient has not done so already, he or she removes the cap 14 to expose the hypodermic needle 52 and inserts the needle at an appropriate location to perform an intramuscular injection of insulin. The insulin injection mechanism preferably includes a sensor that senses when the needle 52 has penetrated the patient's skin and begins a countdown in one-second intervals. The second numeric field 234 accordingly decrements from "5" to "0," during which time the injection mechanism administers the prescribed insulin dosage that was previously displayed. The speaker 18 may accompany the visual countdown on the display with an audible countdown. When the count reaches "0," the second text field displays the message "REMOVE NEEDLE" (not shown in the figures) and the same message is repeated audibly by the speaker 18. When the needle is removed, the injection mechanism provides a signal to the microprocessor indicating a completed insulin injection, which in turn triggers a positive response in step S164.

The time period set in step S162 should be of sufficient duration to permit the user to administer an insulin injection according to this description. A suitable time period will preferably be about five minutes, but can be any appropriate time period between say, three minutes and 10 minutes. If the unit detects an insulin injection before the time period expires, the LCD display 200 changes to the screen shown in display status box D116. It shows the detected blood glucose level as in display status box D114, and the second text field 234 in FIG. 7 reads "RETEST BLOOD IN 15 MIN." Next, the flag status is set to F=1 in step S170 and another time period is set to permit the user to complete the instructed blood test. The process then proceeds to step S174 to await receipt of a blood sample within the allotted time, as represented by the loop containing steps S174 and S176. If no blood test is detected within the allotted time, the unit proceeds to step S168, in which the unit places an automatic call to the emergency service provider so that it can be confirmed that the user is not in danger. These steps S174, S176, and S168 are analogous to steps S130, S132, and S134 discussed above, and the comments relating to that part of the process and possible alternate embodiments, such as providing separate time periods for the waiting period and the blood testing operation, apply equally here.

In an alternate embodiment, the user manually controls the insulin injection using the input device 102. In this embodiment, moving the mode switch 108 to the INJECT INSULIN position activates the input device 102 to permit the user to confirm needle insertion and the completion of an injection. That is, instead of having a sensor that senses when the needle has penetrated the user's skin, the user simply presses any place on the input device 102 to confirm that the unit is in position to administer the desired insulin injection. Likewise, once the injection is complete and the user has withdrawn the needle, pressing any place on the input device signals to the unit software that an insulin injection is complete. While not as independent of user input as the embodiment described above, an this alternate embodiment will undoubtedly prove less expensive to manufacture and thus be more attractive economically for some users.

If a blood sample is taken within the allotted time, the process returns to step S144. If the user's blood glucose level is within the normal range, the process ends at step S146. However, if the patient is still hyperglycemic after the insulin injection, the process proceeds to step S148 to determine if the hyperglycemia is severe (blood glucose greater than L4). If so, step S150 determines that the flag status is F=1 (step S170), and places an automatic call to the subscriber service in step S178. This call will typically include information on the patient's blood glucose level and indicate that an insulin injection has been administered within the preceding 15 minutes. The subscriber service will place a call to the user to confirm that he or she is not in danger.

If the patient's blood glucose level is only mildly elevated (that is, greater than L3 but not greater than L4), the process proceeds to step S160, which detects that the flag status is F=1 (step S170). In this case, the unit terminates the process in step S180.

One of the advantages of being able to store and guide the user through a detailed treatment protocol like that depicted in FIG. 6 and described above is that it enables matching a patient's self-treatment protocol to inpatient treatment protocols. For example, if a detailed treatment protocol is determined for a particular diabetes patient in an inpatient setting, this protocol can be duplicated by appropriate programming of the microprocessor of a unit according to the invention. This streamlines the user's care and increases the utility of the unit because the user-patient's outpatient treatment protocol (using the unit 10) and established inpatient treatment protocol will be essentially the same. This can be expected to reduce the number of times the unit performs emergency notifications, and likewise reduce the number of times a user must be taken to a hospital emergency room because his or her symptoms have become too severe for self-treatment.

Data Recording and Utilization

Another aspect of the invention involves storage in the microprocessor's ROM of complete information regarding the timing and results of the blood glucose testing, times and amounts of blood glucose producing substances ingested, times and amounts of insulin injections, calls to 911 and the subscriber service, or any other aspect of the process just described. For example, the unit can record the time of every glucose test and the resulting glucose level. It can also record whether any alarm condition was encountered. Likewise, the unit can further store each calculated insulin dosage, as well as the actual insulin dosage administered by the patient and time of administration.

The patient's healthcare provider can download this information into a central computer using the USB port 22 or a Wi-Fi connection, and employ it for various reasons. For example, one important use of this information is to make any necessary adjustments to the patient's treatment protocol, which can then be uploaded to the unit as discussed above. The same information, collected from numerous patients, can be used for public health purposes by converting it to statistical information on diabetes treatment.

This data can also have significant commercial uses. For example, diabetes is the subject of frequent clinical trials, which require judicious selection of test subjects to match the particular characteristic of the disease being studied in a given trial. This often requires detailed knowledge of the treatment history of a potential subject, as well as his or her responsiveness to any given treatment regimen. The storage of all of the above information regarding a user of the unit 10 greatly facilitates screening and selection of possible subjects for such clinical trials. Another possible use of the recorded data would be to target training and informational materials specific to particular aspects of the treatment and symptoms of groups of users. For example, a given group of users might be identified as having a certain class of symptoms about which recent research has discovered new information. A healthcare provider could offer as a service the transmission of messages (via cellular telephone) to those users whose treatment profiles warrant. The message could be in the form of a notice for display on the LCD displays of these users' units that additional information they could find helpful or useful, or even critical, can be found at a certain website.

Those skilled in the art will recognize that other variations on the disclosed embodiments that would fall within the scope of the invention are possible. For example, even though the input devices 102 and 106 provide a sleek, streamlined appearance to the unit, mechanical switches can be used to perform the same functions. In another variation, the testing/treatment history of a user can be downloaded via a bar code displayed on the LCD display 200 rather than by using an external USB drive or an Internet connection. In this variation, the unit software can include an algorithm that converts recorded data into a bar code format that is then displayed on the LCD display. Scanning the bar code transfers the information to the scanning device. If necessary, the information can be contained in multiple bar code displays, which are then scanned in turn.

In another alternate embodiment, the unit can include a removable USB storage device on which the data is recorded. This will facilitate manipulation and transportation of the recorded information. For example, it will eliminate an intermediate step in which the unit must be connected to a computer through a USB port, as discussed. It will also enable a user to mail or otherwise transport the recorded data to a healthcare provider, for those users not comfortable with transmitting data over the Internet, as well as eliminating the need to visit the healthcare provider simply to have the recorded data downloaded onto a computer at the provider's location. If a removable USB storage device is used, the unit can be provided with multiple such devices so that the user has a supply on hand.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A portable blood glucose monitoring device and insulin administering pen integrated into a single unit for testing and treating diabetes symptoms in a patient, the unit comprising:

a housing of a size suitable for transport in a handbag or clothing pocket;

a blood glucose monitoring system in said housing for receiving a biological sample from the patient, said blood glucose monitoring system being operable to detect the patient's blood glucose level from the biological sample;

an insulin administration mechanism in said housing for administering an insulin dosage to the patient;

a microprocessor in said housing for determining a detected blood glucose level above a predetermined threshold indicating a hyperglycemic condition of potential danger to the patient and calculating an insulin dosage appropriate to the detected blood glucose level, wherein said insulin administration mechanism is operable to initiate an insulin dosage administration operation and thereafter provide a termination signal to said microprocessor indicating that an insulin dosage has been administered;

a display on said housing for displaying at least one of the detected blood glucose level and the calculated insulin dosage;

a timer in said housing operable to monitor the amount of time elapsed from initiation of the insulin dosage administration operation; and a communication device in said housing and under the control of said microprocessor, wherein in the absence of receipt of said termination signal by said microprocessor after elapse of a predetermined time interval from the initiation of the insulin dosage administration operation, said microprocessor is operable to cause said communication device to automatically inform a remote emergency service provider of a hyperglycemic condition of potential danger to the patient as determined by said microprocessor.

2. A unit as in claim 1, further comprising:

a mode switch in said housing having a first state for actuating said blood glucose monitoring system to cause detection of the glucose level in the received biological sample and a second state for initiating an insulin dosage administration operation; and at least one manual input device operable by a user in conjunction with information displayed on said display for providing a user interface permitting the user to set an insulin dosage that is changed from the calculated insulin dosage displayed on said display, wherein when said mode switch is in said second state said insulin administration mechanism is operable to administer the different insulin dosage when the calculated insulin dosage has been changed and to administer the calculated insulin dosage when it has not been changed.

3. A unit as in claim 2, wherein:

said mode switch is manually operable between its first and second states;

said insulin administration mechanism further includes an administration device through which the insulin can be introduced internally of the patient when said administration device is in place in contact with the patient; and manually setting said mode switch to the second state automatically initiates the insulin dosage administration operation, said unit further comprising:

a sensor for generating a sensing signal when said administration device is in place in contact with the patient for introducing insulin internally of the patient through said administration device; and circuitry in said housing responsive to said sensing signal for automatically administering a dosage of insulin to the patient through said administration device when said sensor indicates that said administration device is in place in contact with the patient.

4. A unit as in claim 3, wherein said administration device includes a hypodermic needle for injecting the insulin dosage and said sensor generates said sensing signal when said needle has penetrated the skin of the patient.

5. A unit as in claim 3, wherein said mode switch has a neutral state and said microprocessor displays a prompt on said display instructing the user to take a biological sample and detect the patient's blood glucose level therefrom when said mode switch is moved from its neutral state to its first state.

6. A unit as in claim 3, wherein receipt by said microprocessor of an actuating signal when said switch is in the second state changes said display to indicate a time interval during which the insulin dosage will be automatically administered.

7. A unit as in claim 6, wherein said administration device includes a hypodermic needle for injecting the insulin dosage and said sensor generates said sensing signal when said needle has penetrated the skin of the patient.

8. A unit as in claim 2, wherein said microprocessor further includes dose lock software that causes said display to display a prompt requiring the user to confirm the desire to change the amount of insulin to be administered before permitting said insulin administration mechanism to automatically administer the amount of insulin input by the user.

9. A unit as in claim 2, wherein:

said unit stores information regarding a particular patient's treatment requirements and said microprocessor determines treatment regimens specific to the particular patient based on the detected blood glucose level and the stored information;

said treatment regimens include (i) ingestion of at least one blood glucose producing substance when the detected blood glucose level indicates that the patient is hypoglycemic, and (ii) administration of insulin when the detected blood glucose level indicates that the patient is hyperglycemic; and said microprocessor causes said display to indicate at least one of (i) an amount of the at least one blood glucose producing substance to be consumed, (ii) the calculated insulin dosage, and (iii) the different insulin dosage.

10. A unit as in claim 1, wherein said communication device includes a cellular telephone and the remote emergency service provider is at least one of a public emergency service provider and an emergency service to which a user of the unit has subscribed.

11. A unit as in claim 10, wherein said communication device is at least one of (i) circuitry within said housing for establishing a wireless connection to a cellular telephone separate from said housing, and (ii) cellular telephone circuitry within said housing.

12. A unit as in claim 1, further comprising circuitry in said housing for detecting the location of the unit, wherein said communication device transmits information regarding the location to the remote emergency service provider.

13. A unit as in claim 12, wherein said circuitry for detecting the location of the unit comprises a GPS receiver.

14. A unit as in claim 1, wherein said unit stores information regarding a particular patient's treatment requirements and said microprocessor is operable to determine treatment regimens specific to the particular patient based on the detected blood glucose level and the stored information and to display the treatment regimens on said display.

15. A unit as in claim 14, wherein said treatment regimens include ingestion of at least one blood glucose producing substance in an amount calculated by said microprocessor based on the detected blood glucose level when the detected blood glucose level indicates that the patient is hypoglycemic; and administration of the calculated insulin dosage determined by said microprocessor based on the detected blood glucose level when the detected blood glucose level indicates that the patient is hyperglycemic.

16. A unit as in claim 1, further including a speaker in said housing connected to said microprocessor for providing voice messages to a user of the unit during operation thereof.

17. A unit as in claim 1, further including a storage device for storing the times of multiple administrations of medication doses and the corresponding medication dosages administered using the unit.

18. A unit as in claim 2, wherein at least one of said mode switch and said manual input device is controlled by touch.

19. A unit as in claim 17, wherein said communication device is operable to provide information in said storage device to a computer accessible to a healthcare provider of the patient.

20. A unit as in claim 1, wherein the biological sample is the blood of the patient.

\* \* \* \* \*